United States Patent [19]

Vieu et al.

[11] 4,203,315
[45] May 20, 1980

[54] REFERENCE PART, ESPECIALLY FOR NONDESTRUCTIVE TESTING BY ULTRASONIC VIBRATIONS, AND A METHOD FOR THE FABRICATION OF SAID PART

[75] Inventors: Alain Vieu, Longueil Ste. Marie; Christian Flambard, Aumont-Senlis, both of France

[73] Assignees: Framatome, Courbevoie; Centre Technique des Industries Mechaniques, Senlis, both of France

[21] Appl. No.: 27,985

[22] Filed: Apr. 6, 1979

[30] Foreign Application Priority Data

Apr. 19, 1978 [FR] France ................................ 78 11474

[51] Int. Cl.² ........................................... G01N 29/04
[52] U.S. Cl. .................................................... 73/1 R
[58] Field of Search .................... 73/1 R, 1 DV, 598

[56] References Cited

U.S. PATENT DOCUMENTS

| 3,608,352 | 9/1971 | Walton et al. | 73/1 R |
| 3,908,439 | 9/1975 | Pelak | 73/1 R |
| 3,933,026 | 1/1976 | Ham | 73/1 R |

Primary Examiner—S. Clement Swisher
Attorney, Agent, or Firm—McDougall, Hersh & Scott

[57] ABSTRACT

One or a number of inserts are each fitted within a housing formed in a reference part, each insert being preferably of cylindrical shape and having a predetermined defect in density. An intimate metallurgical bond is formed between the surface of the insert and the housing by depositing a layer of copper on a steel insert when the part is of steel, and by applying a heat treatment. The reference part serves to calibrate testing instruments for ultrasonic metal inspection as well as to determine the character and size of detected defects in density.

12 Claims, 3 Drawing Figures

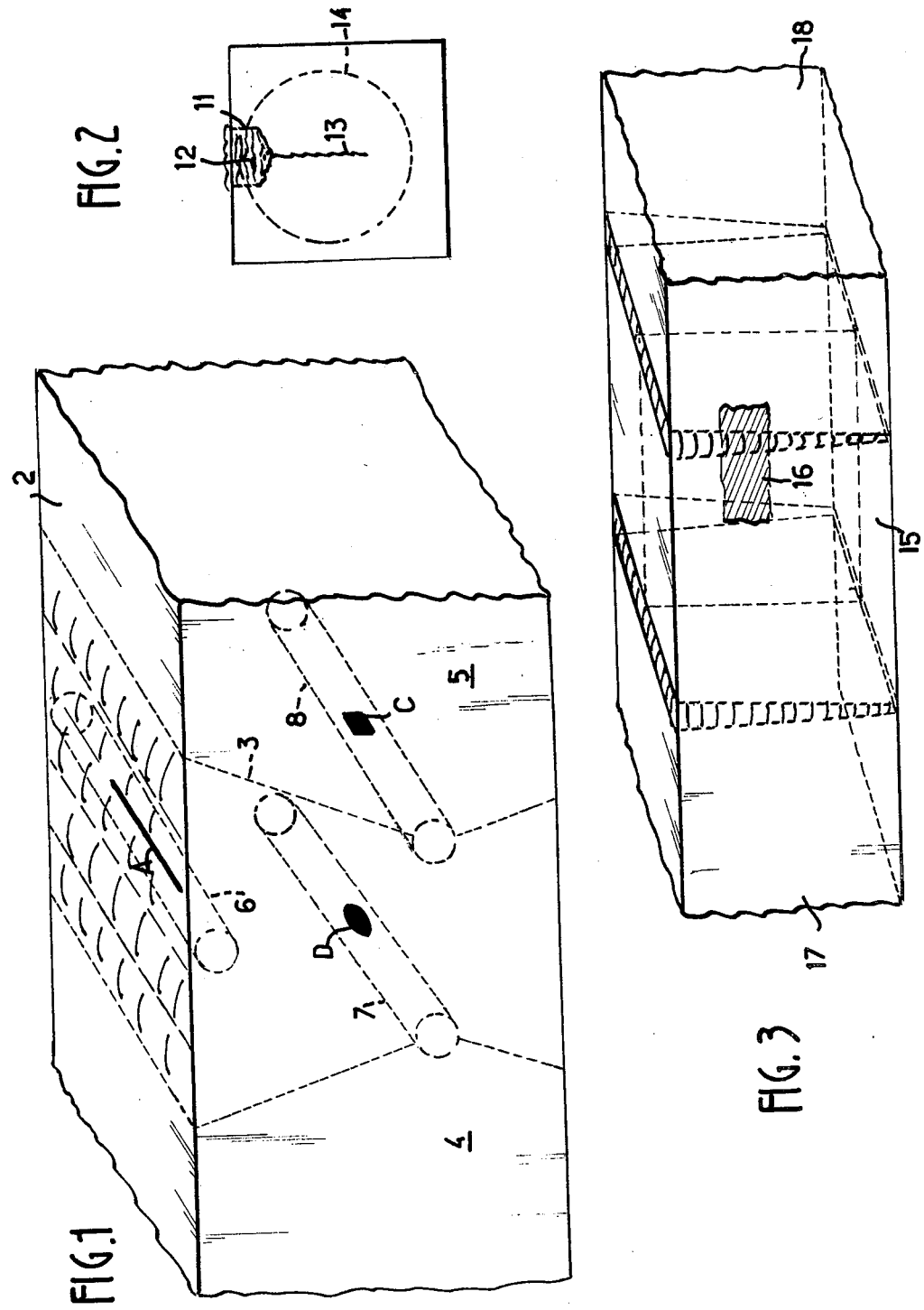

REFERENCE PART, ESPECIALLY FOR NONDESTRUCTIVE TESTING BY ULTRASONIC VIBRATIONS, AND A METHOD FOR THE FABRICATION OF SAID PART

This invention relates to the fabrication of reference parts for use in nondestructive inspection and testing of mechanical parts, more specifically in ultrasonic inspection operations.

Nondestructive testing techniques involving the application of ultrasonic waves are widely employed. These techniques often call for a comparison between the results of measurements performed on the parts to be inspected and the results also obtained in respect of known defects or flaws which have been determined. The aim of this comparison is to calibrate the testing instrument in order to define its detection sensitivity as well as to permit the possibility of determining the nature and size of a defect in density, the presence of which is detected in parts under inspection. It can prove useful in such a case to make provision for a reference part which is similar to the parts under inspection but contains a flaw of known type which is purposely formed in the reference part and perfectly defined by preliminary inspection.

By virtue of the present invention, predetermined flaws, designated hereinafter as defects, can now be placed within reference parts having any shapes and even substantial dimensions. The invention also makes it possible to choose at will, not only the nature, the shape and size of defects, but also their positions within the part both in orientation and in depth, this being achieved with a high degree of accuracy. These aims are particularly important in the field of nondestructive testing by means of ultrasonic vibrations. For this reason, the invention is more especially directed to applications in this field but it must be understood that these applications are not intended to imply any limitation and that the reference part in accordance with the invention and the method of fabrication of said part can also be employed in other fields without thereby departing from the scope of the invention.

A reference part in accordance with the invention which is primarily applicable to nondestructive testing by ultrasonic vibrations is essentially fitted with at least one element having a surface of revolution and especially a cylindrical or conical surface. Said element is provided with a predetermined defect and is inserted in the part so as to be applied in intimate contact with this latter around its entire periphery.

The invention is also directed to a method of fabrication of a reference part, especially a reference part for nondestructive testing and more especially nondestructive testing by ultrasonic vibrations. The method essentially consists in preparing an element of the same material as the part but containing a defect of predetermined density and having a surface of revolution, and in introducing said element as an insert into a housing of complementary shape which has previously been formed within the part. The element having a predetermined defect is thus inserted within the mass of the part to a greater or lesser depth. By subjecting the complete assembly to heat treatment and metal diffusion, an intimate metallurgical bond can then be formed between the part and the insert around the entire periphery of this latter.

In order to obtain an intimate bond between the part and the insert, any known metallurgical technique can in fact be adopted. In particular, surface treatments for producing a uniform, homogeneous and smooth finish can advantageously be applied to the two surfaces of the part and of the element which come into mutual contact at the level of said bond. However, the specific requirements of acoustic inspections have led to the development of a particularly suitable series of operations in accordance with characteristic features of preferred embodiments of the invention.

Thus an intermediate metallic layer which improves the bond mentioned above can advantageously be formed on at least one of the surfaces of the part and of the insert respectively, which contribute to the formation of the intimate bond. To this end, said intermediate layer is selected from a relatively malleable metal designed to form a thin flat element which is also capable of producing good acoustic transmission for the material in which it is placed, namely the material of the part in the case under consideration. This transmission must preferably be such that the ratio of the transmitted energy to the incident energy is higher than 0.9. In the practical application of the method, said intermediate layer is advantageously placed prior to insertion around the entire periphery of the defect-containing element, preferably by means of a conventional method of surface coating such as electrodeposition or sputtering.

In the most frequent case of steel parts, it has been found particularly advantageous to make use of an intermediate layer of copper. The thickness of this layer can be especially within the range of 1 micron to 200 microns and preferably of the order of 30 to 60 microns, taking into account the vibration frequencies usually employed. Instead of copper, it would be feasible to employ other metals such as nickel and silver which also meet the requirements of acoustic transmission in steel.

The intimate bond between the insert and the reference part itself can also be improved by producing a stress at this level. To this end, the insert can be prepared and machined to a slightly larger dimension than that of the housing which is intended to accommodate said insert. Assembly can be carried out after causing temporary thermal shrinkage of the element by cooling and/or thermal expansion of its housing by heating the part. By way of example, immersion of the insert in liquid nitrogen ensures a sufficient degree of shrinkage to permit tight fitting of an insert having a diameter which is larger than the diameter of the housing by approximately 0.1% in the case of diameters of the order of 20 to 50 mm.

The intimate bond between the surfaces is further improved when the mechanical stress thus obtained is combined with an intermediate layer as defined in the foregoing. After a return to temperature equilibrium, an accommodation of surfaces takes place under the tightening action and as a result of the relative hardness of the materials which are present. The surface accommodation just mentioned arises from phenomena of microcreep of surface irregularities and from plastic flow of the intermediate material. In relation with these phenomena, a suitable surface preparation is intended to reduce defects in shape and to improve surface roughness in order to increase the area of the surfaces which are placed in contact with each other. Finishing operations which are conventional in themselves make it possible to obtain very slight defects in shape such as, for example, a defect in straightness of less than 5 microns over a length of 200 mm as well as very slight values of surface roughness such as, for example, an arithmetical roughness in the vicinity of 0.05 micron Ra.

Another treatment for improving the intimate bond between the insert and the reference part itself consists of a heat treatment applied after complete assembly. Heating to a high temperature makes it possible to ensure diffusion of the metal atoms, thus eliminating voids and residual asperities at the interface. A treatment of this type carried out under vacuum makes it possible to prevent any contamination and also takes part in removal of any traces of oxidation. A suitable temperature can be of the order of 0.7 to 0.8 times the melting temperature of the intermediate metal, namely 700 to 900° C. in the case of copper, for example, and can be applied over a period of 1 to 10 hours.

In order to improve these effects of the thermal diffusion treatment, it is an advantage to interpose between the insert and the part an intermediate medium which is particularly adapted to diffuse into crystalline structures, especially into those of steel. In consequence, when the metal of the intermediate layer which is selected for its mechanical and acoustic properties has a low coefficient of diffusion, especially in the case of copper placed between two steel surfaces, this can be compensated for by covering the intermediate layer itself with a deposit of readily diffusible metal which can nevertheless remain of sufficiently small thickness to avoid any appreciable interference with acoustic transmission within the completed reference part. By way of example, there will be employed a nickel deposit having a thickness of the order of one micron on an intermediate copper layer in the case of a steel part.

The effectiveness of a heat treatment of this type can also be improved by means of a suitable choice of treatments to which the surfaces are subjected prior to assembly. For example, cold work of the type which can be obtained by burnishing thus promotes multiplication of vacancies and dislocations through which the metal atoms can migrate more readily at the time of heating.

The elements introduced as inserts into the reference part in accordance with the invention have at least one predetermined defect, that is to say in particular a defect in density within the material which produces a characteristic response in ultrasonic inspection tests. These elements themselves can be formed and prepared in accordance with any known technique. Generally speaking, it is known to produce all kinds of defects in test-pieces having small dimensions. But the present invention has an advantage in that this test-piece need have no dimensional relationship with the completed reference part. Its shape itself can be adapted to the operation which produces the defect, the insert which contains said defect being then cut from the test-piece. In the same manner, it is also possible to take a defect which has appeared accidentally within a part under inspection. In all cases, the arrangement of the defect within the reference part can be varied at will, especially its angle of inclination and its location, either by modifying the arrangement of the defect within the completed element or in the arrangement of the insert and of its housing within the reference part.

It should be pointed out that, for the fabrication of elements to be inserted into the reference parts, recourse can be had to techniques which are conventional per se and especially to techniques which make it possible to form an intimate metallurgical bond between two flat surfaces of blocks having small dimensions. For example, it is thus possible to make use of diffusion welding in order to join two blocks together and enclose a predetermined defect between them. In another example, two blocks each having a predetermined defect can be butt-welded by the electron beam process, thus forming an insert containing a plurality of defects.

Some of the possible variants in the practical application of the invention will become more readily apparent from the following description of a particular example of embodiment. This example is not given in any limiting sense and relates to the application of the invention to the fabrication of a reference part for ultrasonic inspection, this part being provided with a plurality of inserts which simulate the presence of flaws within a welded joint.

Reference will be made in the following description to the accompanying drawings, wherein:

FIG. 1 shows diagrammatically a complete reference part in accordance with the invention;

FIG. 2 illustrates more especially the formation of one of the defects introduced into the reference part of FIG. 1;

FIG. 3 illustrates the fabrication of another element having a predetermined defect for the same reference part.

The reference part shown in FIG. 1 is of steel or carbon and is so designed as to simulate a part of large size containing a weld bead which in turn contains defects of density. A study of these defects must be made from the external inspection face constituted by the top face 2 in the figure, this being performed by means of any of the known methods entailing the use of ultrasonic wave beams. There have been shown in dashed lines the limits 3 of an imaginary weld bead or fillet between two portions 4 and 5. The part can have any shape or contour. In the particular case under consideration, the part consists of a parallelepipedal block having a length of 1400 mm and a cross-section of 250 ×200 mm at the level of the postulated weld bead.

In the particular case of the example, it has been postulated that three defects are to be formed within the reference part. These defects are as follows:

Defect A: a crack having a width of 10 mm and a length of 100 mm, which is perpendicular to the plane of the top inspection surface and located at a distance of 5 mm from said surface;

Defect B: flat defect of elliptical shape having a major axis of 25 mm, a minor axis of 15 mm, a thickness of the order of 10 $\mu$m, placed at approximately 160 mm beneath the top surface 2, centered within the thickness of the part, and so oriented that the plane of the defect has an orientation of 10° with the top plane of the part and 80° with the plane of a lateral face;

Defect C: flat defect of rectangular shape measuring 10×30 mm, having a thickness of 10 $\mu$m, simulating a bonding defect, placed at approximately 160 mm beneath the top surface of the part, centered within the thickness of said part, and so oriented that the plane of said defect coincides with the imaginary weld plane.

These three defects are present respectively in three inserts 6, 7, 8 placed within corresponding housings of the reference part. Each insert has the shape of a cylinder which occupies a cylindrical housing having an axis which is not perpendicular to the top face 2 and extends through the entire thickness of the part.

The housings are formed by boring through the block which constitutes the reference part. The housings which are intended to receive the inserts 6 and 8 are perpendicular to the lateral faces of the part whilst the housing which is intended to receive the insert 7 is oblique according to the desired angle of inclination of the defect D. The orientation of the flat defect C is obtained as a result of the angular orientation of the insert 8 within its housing.

The conditions of machining of the housings are, for example, as follows:

Drilling and reaming to the diameter of 31.5 mm, the geometrical error over the entire length being smaller than 5 $\mu$m (error of shape), the surface roughness being in the vicinity of 1 $\mu$m Ra;

Burnishing: the operation is performed, for example, on a lathe or alternatively on a drilling machine by means of a tool of the type which comprises tapered rollers and is introduced into the bore in rotational motion; this operation must be performed in such a manner as to obtain surface work-hardening and a degree of surface roughness which is lower than 0.1 $\mu$m Ra.

Each insert is taken from a parallelepipedal block which contains the corresponding defect and is machined so as to obtain a cylindrical part which is rough-turned to a diameter of 32 mm.

In order to form the defect A, the operation can consist of a bending fatigue test on a notched testpiece. The fatigue test is continued until a crack is formed to the desired depth (10 mm in this instance). A block cut-out of said test-piece and containing the full length of the crack is extended to the length of the insert by electron beam welding of two steel blocks respectively at each end, the quality and grade of steel being identical in both cases. The complete block thus obtained is subjected to a thermal treatment in an oxidizing atmosphere (R) for a period of one hour at 850° C. The aim of this treatment is to oxidize the internal surfaces of the crack in order to prevent re-welding of the two lips of said crack in the event of subsequent closure and to homogenize the zones which have been welded by the electron beam process. The V-notch into which the crack opens is then re-cut by milling to a rectangular cross-section as shown at 11 in FIG. 2, then plugged with a weld fillet 12. The crack is shown at 13 in FIG. 2. The cylindrical insert is then turned on a lathe to produce the cross-section shown in the figure at 14.

The flat defects B and C are formed at the interface of two blocks which are welded together by diffusion, at least one of the blocks having previously been treated so as to form the defect. The defect B is obtained by chemical etching of one face to a depth of 10 microns with an elliptical surface having the desired dimensions. In the case of the defect C, one face is machined by the spark erosion process over a parallelepipedal surface to a depth of 10 to 20 microns with a state of surface of at least 200 microns Ra. An element shown at 15 in FIG. 3 and containing the defect 16 is taken from the assembly which is obtained by welding of the two initial blocks. In order to obtain the total length of the insert, two elements 17 and 18 of steel having the same quality and grade are abuttingly applied on each side of the element 15 and welded to this latter by the electron beam process. After heat treatment at 850° C. for a period of one hour so as to ensure homogeneity of the structure, the blank of the cylindrical insert containing the defect 16 is machined in the block thus obtained.

In order to be placed within its housing within the reference part, each insert undergoes a series of treatments. It is first ground to a diameter of 31.48 mm, the state of surface being approximately 0.2 $\mu$m Ra. It is then subjected to a surface treatment in an electrolytic bath so as to receive a copper coating having a thickness of 100 $\mu$m which is free of any defect. When the final value of compression (hoop stress) between the insert and the part has been chosen, the dimension of the insert is defined as a function of said compression, taking into account the dimension of the bore (to within a tolerance of $\mu$m). The insert is machined by grinding so as to obtain a defect in shape which remains smaller than 2 $\mu$m over a length of 200 mm and a degree of surface roughness which is better than 0.1 $\mu$m Ra.

Positioning of the insert within the reference part is carried out by increasing the temperature difference between the two parts to the greatest possible extent, the object of this difference being to reduce the geometrical dimensions of the insert with respect to the dimensions defining the bore which constitutes the insert housing.

The ultimate preparation which precedes positioning of the insert within the part is as follows:

Pickling of the insert: the pickling operation is performed with a view to scouring the surface of the insert and consists of electrolytic action in an alkaline bath, the insert being brought to a positive potential and allowed to remain immersed in the solution for a period of approximately 5 minutes;

Coating: the insert is provided if necessary on the intermediate copper layer with a thin nickel deposit (of the order of one $\mu$m) obtained by electrolytic treatment;

Heating-up: the insert is dried and immersed in liquid nitrogen; the immersion is continued in order to allow the material to attain the equilibrium temperature of liquid nitrogen, namely $-196°$ C.;

Scouring of the housing: the reference part is cleaned by immersion in a trichloroethylene bath under the action of ultrasonic vibrations at a frequency of 25 kHz;

Heating-up: the baths which serve to clean the reference part are heated to the boiling point of the solvent employed, thus making it possible to withdraw the part for the final operation at a temperature of approximately 40° C. to 50° C.

Under these temperature conditions, the inserts are introduced into the corresponding bores by hand; they are oriented by following reference marks previously placed on the parts in order to ensure suitable orientation of the defects contained therein. These operations are carried out over a very short time interval of a few seconds from the moment of withdrawal of the insert from the liquid nitrogen bath.

In order to promote cohesion between the surfaces of the assembled parts, the complete assembly is subjected to a heat treatment carried out in vacuo for a period of 10 hours at a temperature of 750° C.

In the reference part which has thus been finally obtained, the intimate metallurgical bond formed between the inserts and the material of the part itself as a result of a combination of the different treatments and/or a suitable choice of materials employed is such that the bond has practically no incidence on the results of ultrasonic inspection tests performed in order to detect the defects.

It must naturally be understood, however, the reference part hereinabove described by way of example is not intended to imply any limitation whatsoever and that the invention extends on the contrary to all alternative forms of a part of this type as well as to all variants of the method of fabrication of said part.

What is claimed is:

1. A reference part, especially for nondestructive testing by ultrasonic vibrations, wherein said part is fitted with an element having a surface of revolution and provided with a predetermined defect, said element being inserted within said part so as to be applied in intimate contact therewith around its entire periphery.

2. A reference part as claimed in claim 1, wherein said part comprises an intermediate layer for ensuring said intimate contact, said intermediate layer being formed of a relatively malleable metal having good characteristics of ultrasonic-vibration transmission into the material of the part.

3. A reference part as claimed in claim 2, wherein the intermediate layer is of copper having a thickness of the order of 1 to 200 microns in the case of a steel part containing a steel element or insert.

4. A reference part as claimed in claim 2, wherein said intermediate layer formed on said element or insert is further provided with a deposit of readily diffusible metal which has been subjected to a treatment consisting of metallic diffusion into the material of the part, said deposit being especially of nickel on an intermediate layer of copper.

5. A reference part as claimed in claim 1, wherein said element or insert is of cylindrical shape.

6. A method of fabrication of a reference part as claimed in claim 1, wherein said method essentially consists in preparing an element of the same material as the part and containing a predetermined defect in density, in providing said element with a surface of revolution and especially a cylindrical surface, in introducing said element in the form of an insert within a housing of complementary shape formed beforehand within the part and in forming an intimate metallurgical bond between the part and the insert around the entire periphery of said insert.

7. A method as claimed in claim 6, wherein an intermediate layer of a relatively malleable metal having good characteristics of acoustic transmission into the material of the part and consisting especially of copper in the case of a steel part is formed prior to insertion on at least one of the surfaces which take part in said intimate bond and preferably on said element.

8. A method as claimed in claim 6, wherein the diameter of said element is at least equal to and preferably slightly larger than that of said housing and that thermal shrinkage of the element and/or thermal expansion of the housing is carried out in order to permit insertion of the element within said housing.

9. A method as claimed in claim 6, wherein the part is subjected to a heat treatment for metallic diffusion between the contact surfaces of said part and the element after insertion of said element within its housing.

10. A method as claimed in claim 9, wherein the intermediate layer is coated with a deposit of readily diffusible metal, said deposit being especially of nickel on an intermediate layer of copper.

11. A method as claimed in claim 8, wherein said method comprises the insertion of a plurality of similar elements containing defects within any one housing of the part, said elements being joined together in end-to-end relation on flat faces, for example by welding and especially by electron beam welding.

12. A method as claimed in claim 8, wherein the reference part is provided with one or a number of housings for receiving elements containing defects having axes which are not parallel to an external ultrasonic inspection face.

* * * * *